US008725257B2

(12) United States Patent
Maskara et al.

(10) Patent No.: US 8,725,257 B2
(45) Date of Patent: May 13, 2014

(54) DYNAMIC CARDIAC RESYNCHRONIZATION THERAPY BY TRACKING INTRINSIC CONDUCTION

(71) Applicant: Cardiac Pacemakers, Inc., Saint Paul, MN (US)

(72) Inventors: Barun Maskara, Blaine, MN (US); Jiang Ding, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/686,352

(22) Filed: Nov. 27, 2012

(65) Prior Publication Data

US 2013/0085539 A1  Apr. 4, 2013

Related U.S. Application Data

(62) Division of application No. 12/570,167, filed on Sep. 30, 2009, now Pat. No. 8,321,014.

(60) Provisional application No. 61/195,275, filed on Oct. 6, 2008.

(51) Int. Cl.
*A61N 1/00* (2006.01)

(52) U.S. Cl.
USPC .......................................................... 607/9

(58) Field of Classification Search
CPC .. A61N 1/36114; A61N 1/3627; A61N 1/362
USPC .......................................................... 607/9
See application file for complete search history.

(56) References Cited

U.S. PATENT DOCUMENTS

| 3,920,005 | A | 11/1975 | Gombrich et al. |
| 4,388,927 | A | 6/1983 | Schober |
| 4,953,551 | A | 9/1990 | Mehra et al. |
| 5,133,353 | A | 7/1992 | Hauser |
| 5,170,784 | A | 12/1992 | Ramon et al. |
| 5,179,945 | A | 1/1993 | Van Hofwegen et al. |
| 5,209,229 | A | 5/1993 | Gilli |

(Continued)

FOREIGN PATENT DOCUMENTS

| EP | 0468720 | 1/1992 |
| EP | 0560569 | 9/1993 |

(Continued)

OTHER PUBLICATIONS

Office Action dated May 15, 2012 with translation from JP Application No. 2009-518259, 4 pages.

(Continued)

*Primary Examiner* — Christopher D Koharski
*Assistant Examiner* — Philip Edwards
(74) *Attorney, Agent, or Firm* — Brooks, Cameron & Huebsch, PLLC

(57) ABSTRACT

Systems and methods for pacing the heart using resynchronization pacing delays that achieve improvement of cardiac function are described. An early activation pacing interval is calculated based on an optimal AV delay and an atrial to early ventricular activation interval between an atrial event and early activation of a ventricular depolarization. The early activation pacing interval for the ventricle is calculated by subtracting the measured $AV_{EA}$ from the calculated optimal AV delay. The early activation pacing interval is initiated responsive to sensing early activation of the ventricle and pacing is delivered relative to expiration of the early activation pacing interval.

8 Claims, 8 Drawing Sheets

(56) References Cited

U.S. PATENT DOCUMENTS

| | | |
|---|---|---|
| 5,222,493 A | 6/1993 | Sholder |
| 5,231,990 A | 8/1993 | Gauglitz |
| 5,261,400 A | 11/1993 | Bardy |
| 5,271,411 A | 12/1993 | Ripley et al. |
| 5,292,338 A | 3/1994 | Bardy |
| 5,300,106 A | 4/1994 | Dahl et al. |
| 5,312,445 A | 5/1994 | Nappholz et al. |
| 5,314,430 A | 5/1994 | Bardy |
| 5,314,459 A | 5/1994 | Swanson et al. |
| 5,318,597 A | 6/1994 | Hauck et al. |
| 5,331,966 A | 7/1994 | Bennett et al. |
| 5,331,996 A | 7/1994 | Ziehm |
| 5,333,095 A | 7/1994 | Stevenson et al. |
| 5,342,402 A | 8/1994 | Olson |
| 5,350,410 A | 9/1994 | Kieks et al. |
| 5,372,606 A | 12/1994 | Lang et al. |
| 5,376,106 A | 12/1994 | Stahmann et al. |
| 5,411,525 A | 5/1995 | Swanson et al. |
| 5,411,533 A | 5/1995 | Dubreuil |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,468,254 A | 11/1995 | Hahn et al. |
| 5,520,191 A | 5/1996 | Karisson et al. |
| 5,531,779 A | 7/1996 | Dahl et al. |
| 5,605,158 A | 2/1997 | Snell |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittman et al. |
| 5,662,688 A | 9/1997 | Haefner et al. |
| 5,674,254 A | 10/1997 | van Krieken |
| 5,683,431 A | 11/1997 | Wang |
| 5,683,434 A | 11/1997 | Archer |
| 5,697,953 A | 12/1997 | Kroll et al. |
| 5,697,959 A | 12/1997 | Poore |
| 5,704,365 A | 1/1998 | Albrecht et al. |
| 5,724,984 A | 3/1998 | Arnold et al. |
| 5,735,882 A | 4/1998 | Rottenberg et al. |
| 5,803,084 A | 9/1998 | Olson |
| 5,827,326 A | 10/1998 | Kroll et al. |
| 5,861,013 A | 1/1999 | Peck et al. |
| 5,871,512 A | 2/1999 | Hemming et al. |
| 5,873,898 A | 2/1999 | Hemming et al. |
| 5,895,414 A | 4/1999 | Sanchez-Zambrano |
| 5,957,956 A | 9/1999 | Kroll et al. |
| 5,983,138 A | 11/1999 | Kramer |
| 5,987,352 A | 11/1999 | Klein et al. |
| 6,049,730 A | 4/2000 | Kristbjarmarson |
| 6,084,253 A | 7/2000 | Johnson et al. |
| 6,101,416 A | 8/2000 | Sloman |
| 6,115,628 A | 9/2000 | Stadler et al. |
| 6,128,535 A | 10/2000 | Maarse |
| 6,134,473 A | 10/2000 | Hemming et al. |
| 6,144,880 A | 11/2000 | Ding et al. |
| 6,148,230 A | 11/2000 | KenKnight |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,192,275 B1 | 2/2001 | Zhu et al. |
| 6,227,072 B1 | 5/2001 | Ritchey et al. |
| 6,267,778 B1 | 7/2001 | Cohen |
| 6,275,731 B1 | 8/2001 | Zhu et al. |
| 6,280,462 B1 | 8/2001 | Hauser et al. |
| 6,282,440 B1 | 8/2001 | Brodnick et al. |
| 6,301,503 B1 | 10/2001 | Hsu et al. |
| 6,324,421 B1 | 11/2001 | Stadler et al. |
| 6,324,427 B1 | 11/2001 | Florio |
| 6,351,673 B1 | 2/2002 | Ding et al. |
| 6,360,127 B1 | 3/2002 | Ding et al. |
| 6,409,675 B1 | 6/2002 | Turcott |
| 6,415,174 B1 | 7/2002 | Bebehani et al. |
| 6,424,234 B1 | 7/2002 | Stevenson |
| 6,438,409 B1 | 8/2002 | Malik et al. |
| 6,456,481 B1 | 9/2002 | Stevenson |
| 6,456,880 B1 | 9/2002 | Park et al. |
| 6,491,639 B1 | 12/2002 | Turcott |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,564,106 B2 | 5/2003 | Guck et al. |
| 6,567,701 B2 | 5/2003 | Vonk |
| 6,607,509 B2 | 8/2003 | Bobroff et al. |
| 6,609,027 B2 | 8/2003 | Kroll et al. |
| 6,615,082 B1 | 9/2003 | Mandell |
| 6,615,083 B2 | 9/2003 | Kupper |
| 6,622,046 B2 | 9/2003 | Fraley et al. |
| 6,625,490 B1 | 9/2003 | McClure et al. |
| 6,631,290 B1 | 10/2003 | Guck et al. |
| 6,690,967 B2 | 2/2004 | Meij |
| 6,701,170 B2 | 3/2004 | Stetson |
| 6,725,085 B2 | 4/2004 | Schwartzman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,871,096 B2 | 3/2005 | Hill |
| 6,884,218 B2 | 4/2005 | Olson et al. |
| 6,904,315 B2 | 6/2005 | Panken et al. |
| 6,925,324 B2 | 8/2005 | Shusterman |
| 6,925,330 B2 | 8/2005 | Kleine |
| 6,927,721 B2 | 8/2005 | Ostroff |
| 6,937,907 B2 | 8/2005 | Bardy et al. |
| 6,944,579 B2 | 9/2005 | Shimizu |
| 6,950,702 B2 | 9/2005 | Sweeney |
| 6,950,705 B2 | 9/2005 | Bardy et al. |
| 6,952,608 B2 | 10/2005 | Ostroff |
| 6,952,610 B2 | 10/2005 | Ostroff |
| 6,954,670 B2 | 10/2005 | Ostroff |
| 6,961,619 B2 | 11/2005 | Casey |
| 6,973,350 B1 | 12/2005 | Levine et al. |
| 6,983,264 B2 | 1/2006 | Shimizu |
| 6,988,003 B2 | 1/2006 | Bardy et al. |
| 6,993,379 B1 | 1/2006 | Kroll |
| 6,993,389 B2 | 1/2006 | Ding |
| 7,027,861 B2 | 4/2006 | Thompson |
| 7,027,868 B2 | 4/2006 | Rueter et al. |
| 7,039,459 B2 | 5/2006 | Bardy |
| 7,039,465 B2 | 5/2006 | Bardy |
| 7,043,299 B2 | 5/2006 | Erlinger |
| 7,050,851 B2 | 5/2006 | Plombon et al. |
| 7,065,400 B2 | 6/2006 | Schechter |
| 7,065,407 B2 | 6/2006 | Bardy |
| 7,065,410 B2 | 6/2006 | Bardy et al. |
| 7,069,080 B2 | 6/2006 | Bardy |
| 7,076,296 B2 | 7/2006 | Rissmann et al. |
| 7,079,988 B2 | 7/2006 | Albera |
| 7,090,682 B2 | 8/2006 | Sanders et al. |
| 7,092,754 B2 | 8/2006 | Bardy et al. |
| 7,096,064 B2 | 8/2006 | Deno et al. |
| 7,107,093 B2 | 9/2006 | Burnes |
| 7,110,817 B2 | 9/2006 | Yu et al. |
| 7,120,495 B2 | 10/2006 | Bardy et al. |
| 7,123,960 B2 | 10/2006 | Ding et al. |
| 7,129,935 B2 | 10/2006 | Mackey |
| 7,144,586 B2 | 12/2006 | Levy et al. |
| 7,146,206 B2 | 12/2006 | Glass et al. |
| 7,146,212 B2 | 12/2006 | Bardy et al. |
| 7,149,575 B2 | 12/2006 | Ostroff et al. |
| 7,158,830 B2 | 1/2007 | Yu et al. |
| 7,181,285 B2 | 2/2007 | Lindh |

(56) References Cited

U.S. PATENT DOCUMENTS

| | | |
|---|---|---|
| 7,184,835 B2 | 2/2007 | Kramer et al. |
| 7,194,302 B2 | 3/2007 | Bardy et al. |
| 7,194,309 B2 | 3/2007 | Ostroff et al. |
| 7,203,540 B2 | 4/2007 | Ding et al. |
| 7,228,173 B2 | 6/2007 | Cazares |
| 7,228,174 B2 | 6/2007 | Burnes et al. |
| 7,236,819 B2 | 6/2007 | Brockway |
| 7,242,978 B2 | 7/2007 | Cao |
| 7,245,962 B2 | 7/2007 | Ciaccio et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,299,086 B2 | 11/2007 | McCabe et al. |
| 7,310,554 B2 | 12/2007 | Kramer et al. |
| 7,359,749 B2 | 4/2008 | Quenet et al. |
| 7,457,664 B2 | 11/2008 | Zhang et al. |
| 7,509,170 B2 | 3/2009 | Zhang et al. |
| 7,558,628 B2 | 7/2009 | Yonce et al. |
| 7,580,741 B2 | 8/2009 | Cazares et al. |
| 7,653,431 B2 | 1/2010 | Cazares et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0082658 A1 | 6/2002 | Heinrich et al. |
| 2002/0095184 A1 | 7/2002 | Bardy et al. |
| 2002/0095188 A1 | 7/2002 | Mower |
| 2002/0107544 A1 | 8/2002 | Ostroff et al. |
| 2002/0107545 A1 | 8/2002 | Rissmann et al. |
| 2002/0138111 A1 | 9/2002 | Greenhut et al. |
| 2002/0183798 A1 | 12/2002 | Vonk |
| 2003/0023175 A1 | 1/2003 | Arzbaecher et al. |
| 2003/0050671 A1 | 3/2003 | Bradley |
| 2003/0083710 A1 | 5/2003 | Ternes et al. |
| 2003/0083711 A1 | 5/2003 | Yonce et al. |
| 2003/0100925 A1 | 5/2003 | Pape et al. |
| 2003/0204214 A1 | 10/2003 | Ferek-Patric |
| 2003/0212436 A1 | 11/2003 | Brown |
| 2004/0064159 A1 | 4/2004 | Hoijer et al. |
| 2004/0127950 A1 | 7/2004 | Kim et al. |
| 2004/0158293 A1 | 8/2004 | Yonce et al. |
| 2004/0171959 A1 | 9/2004 | Staler et al. |
| 2004/0215240 A1 | 10/2004 | Lovett et al. |
| 2004/0243014 A1 | 12/2004 | Lee et al. |
| 2005/0010120 A1 | 1/2005 | Jung |
| 2005/0038478 A1 | 2/2005 | Kiepfer et al. |
| 2005/0065587 A1 | 3/2005 | Gryzwa |
| 2005/0107839 A1 | 5/2005 | Sanders |
| 2005/0131480 A1 | 6/2005 | Kramer et al. |
| 2005/0137632 A1 | 6/2005 | Ding et al. |
| 2006/0116593 A1 | 6/2006 | Zhang et al. |
| 2006/0253043 A1 | 11/2006 | Zhang et al. |
| 2006/0259086 A1 | 11/2006 | Yu et al. |
| 2007/0027488 A1 | 2/2007 | Kaiser et al. |
| 2007/0049974 A1 | 3/2007 | Li et al. |
| 2008/0004665 A1 | 1/2008 | McCabe et al. |
| 2008/0009909 A1 | 1/2008 | Sathaye et al. |
| 2008/0097537 A1 | 4/2008 | Duann et al. |
| 2009/0076557 A1 | 3/2009 | Zhang et al. |
| 2009/0198301 A1 | 8/2009 | Zhang et al. |
| 2009/0312813 A1 | 12/2009 | Cazares |

FOREIGN PATENT DOCUMENTS

| | | |
|---|---|---|
| EP | 1038498 | 9/2000 |
| EP | 1350539 | 10/2003 |
| EP | 1629863 | 3/2006 |
| WO | 9217240 | 10/1992 |
| WO | 9220402 | 11/1992 |
| WO | 0240097 | 5/2002 |
| WO | 0247761 | 6/2002 |
| WO | 03003905 | 1/2003 |
| WO | 03028550 | 4/2003 |
| WO | 2005058412 | 6/2005 |
| WO | 2005089865 | 9/2005 |
| WO | 2006065707 | 6/2006 |
| WO | 2008005270 | 1/2008 |

OTHER PUBLICATIONS

Invitation to Pay Fees from parallel International Application No. PCT/US2009/059005 dated Feb. 10, 2010.

International Search Report and Written Opinion dated May 4, 2011 from PCT Application No. PCT/US2009/059005, 14 pages.

International Preliminary Report on Patentability dated May 19, 2011 from PCT Application No. PCT/US2009/059005.

Invitation to Pay Additional Fees dated Feb. 10, 2010 from PCT Application No. PCT/US2009/059005, 5 pages.

Acar et al., "SVD-based on-line exercise ECG signal orthogonalization", IEEE Transactions on Biomedical Engineering, vol. 46, No. 3, Mar. 1999. Abstract only.

Belouchrani et al., "Blind Source Separation Based on Time-Frequency Signal Representations," IEEE Transactions on Signal Processing, vol. 46, No. 11, pp. 2888-2897 (Nov. 1998).

Comon, "Independent component analysis, A new concept?", Signal process, vol. 36, No. 3. pp. 287-314, (Apr. 1994).

Gallois, et al. "Multi-Channel Analysis of the EEG signals and Statistic Particularities for Epileptic Seizure Forecast", Second Joint EMBS/BMES Conference, pp. 208-215 (Oct. 23-26, 2002).

Gradaus et al. "Nonthoracotomy Implantable Cardioverter Defibrillator Placement in Children: Use of a Subcutaneous Array Leads and Abdominally Placed Implantable Cardioverter Defibrilators in Children", J. of Cardiovascular Electrophysiology, vol. 12, No. 3 pp. 356-360 (Mar. 2001).

Hartz, et al., "New approach to Defibrillator Insertion", J. Thoracic Cardiovascular Surgery, vol. 97 pp. 920-922. (1989).

Hyvarinen et al., "Independent Component Analysis: A Tutorial", Helsinski Univ. of Tevhnology, Apr. 1999.

Kolettis, et al., "Submammary Implantation of a Cardioverter-Defibrillator with a Nonthoractomy Lead System," Am. Heart J., vol. 126, pp. 12222-1221 (Nov. 1993).

Krahn. et al. "Recurrent syncope. Experience with an implantable loop record", Cardiol, Clin., vol. 15(2), May 1997, pp. 316-326.

Leng et al. "Lead Configuration for Defibrillator Implantation in a Patient with Congenital Heart Disease and a Mechanical Prosthetic Tricuspid Valve", PACE, vol. 24, No. 8, pp. 1291-1292 (Aug. 2001).

Park el al., "Use of Implantable Cardioverter Defibrillator in an Eight-Month-Old Infant with Ventricular Fibrillation Arising from a Myocardial Fibroma", PACE, vol. 22, No. 1, pp. 138-139 (Jan. 1999).

Rieta et al., "Atrial Activity Extraction Based on Blind Source Separation as an Alternative to QRST Cancellation for Atrial Fibrillation Analysis", Computers in Cardiology, vol. 27, pp. 69-72 (2000).

Schuder et al.,"Experimental Ventricular Defibrillation with an Automatic and Completely Implanted System", Trans. Am. Soc. Artif. Into. Organs, vol. 16, pp. 207-212 (1970).

Schuder et al., "Transthoracic Ventricular Defibrillation in the Dog with Truncated and Untruncated Exponential Stimuli", IEEE Trans. on Bio-Medical Engin., vol. BME-18, No. 6, pp. 410-415 (Nov. 1971).

Schuder et al., "Ventricular Defibrillation in the Dog using Implanted and Partitally Implanted Electrode Systems", Am. J. of Cardiology, vol. 33, pp. 243-247 (Feb. 1974).

Smits et al., "Defibrillation Threshold (DFT) Model of a Fully Subcutaneous ICD System, Europace Supplements", vol. 2, at col. 778, p. B83, Jun. 2001.

Stirbis et al.,"Optimizing the Shape of Implanted Artificial Pacemakers", Kaunas Medical Instute. Translated from Meditsinskaya Tekhnika, No. 6, pp. 25-27 (1986). Abstract only.

Wilkoff et al., "Precenting Shocks after ICD Implantation: Can a Strategy of Standardized ICD Programming Match Physician Tailored?" Late Breaking Trials, HRS (2005). No copy available.

Zarzonso et al., Blind Separation of Independent Sources for Virtually Any Source Probability Density Function, IEEE Transcartions on Signal Processing, vol. 47, No. 9, pp. 2419-2432 (Sep. 1999).

(56) References Cited

OTHER PUBLICATIONS

Zarzonso et al., Noninvasive Fetal Electrocardiogram Extraction: Blind Separation Versus Adaptive Noise Cancellation, IEEE Transactions on Signal Processing, vol. 48, No. 1, pp. 12-18 (Jan. 2001).

International Search Report and Written Opinion for PCT Application No. PCT/US2007/014968, dated Jun. 26, 2007, 15 pages.
International Preliminary Report on Patentability for PCT Application No. PCT/US2007/014968, dated Jan. 6, 2009, 10 pages.
File History for U.S. Appl. No. 11/478,428.
File History for U.S. Appl. No. 11/478,286.

DYNAMIC CARDIAC RESYNCHRONIZATION THERAPY BY TRACKING INTRINSIC CONDUCTION

RELATED APPLICATIONS

This application is a divisional application of U.S. patent application Ser. No. 12/570,167 filed on Sep. 30, 2009, which claims priority from U.S. Provisional Patent Application Ser. No. 61/195,275, filed on Oct. 6, 2008, the entire contents of which are hereby incorporated by reference.

FIELD OF THE INVENTION

The present invention relates generally to cardiac pacing therapy, and more specifically, to methods and systems for dynamically determining timing for the delivery of pacing pulses to achieve cardiac resynchronization.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

Cardiac arrhythmia occurs when the heart rhythm is irregular or if the heart rate is too slow or too fast. During an arrhythmic episode, the heart's pumping action may become impaired and blood flow to peripheral tissues may be inadequate. Cardiac arrhythmias have a number of etiological sources, including tissue damage due to myocardial infarction, infection, or degradation of the heart's ability to generate or synchronize the electrical impulses that coordinate contractions. Bradyarrhythmia occurs when the heart rhythm is too slow. This condition may be caused, for example, by impaired function of the SA node, denoted sick sinus syndrome, or by delayed propagation or blockage of the electrical impulse between the atria and ventricles. Bradyarrhythmia produces a heart rate that is too slow to maintain adequate circulation. Tachyarrhythmia occurs when the heart rate is too rapid. Tachyarrhythmia may have its origin in either the atria or the ventricles. Tachyarrhythmia occurring in the atria of the heart, for example, includes atrial fibrillation and atrial flutter. Both conditions are characterized by rapid contractions of the atria. In addition to being hemodynamically inefficient, the rapid contractions of the atria may also adversely affect the ventricular rate.

Ventricular tachyarrhythmia occurs when electrical activity arises in the ventricular myocardium at a rate more rapid than the normal sinus rhythm. Ventricular tachyarrhythmia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management (CRM) systems have been used as an effective treatment for patients with serious arrhythmias. CRM system operate by delivering relatively high energy electrical shocks to the heart to terminate tachyarrhythmia and/or by delivering relatively low energy electrical pulses to one or more heart chambers, causing the heart chambers to contract at heart rate that is hemodynamically sufficient.

Pacing therapy has also been used to improve cardiac output for patients who suffer from heart failure. Heart failure is frequently related to intraventricular and/or intraventricular conduction defects, e.g., bundle branch blocks which lead to cardiac dyssynchrony and reduced pumping action. To treat heart failure, CRM systems deliver timed pacing pulses that produce more coordinated contractions of the atria and/or ventricles. The pacing pulses are delivered to the heart chambers at specific intervals to achieve optimal improvement in pumping efficiency and cardiac output. Cardiac resynchronization pacing may include pacing both ventricles after a specified atrioventricular delay. The ventricular paces may be delivered simultaneously or separated by a programmable offset.

Appropriate specification of various resynchronization pacing delays is needed to achieve optimal improvement of cardiac function. For the reasons stated above, and for other reasons stated below which will become apparent to those skilled in the art upon reading the present specification, there is a need in the art for methods and systems that provide for determination of timing intervals for cardiac resynchronization therapy. The present invention fulfills these and other needs and provides other enhancements over the prior art.

SUMMARY OF THE INVENTION

Embodiments of the present invention are directed to systems and methods for pacing the heart using resynchronization pacing delays that achieve improvement of cardiac function. One embodiment of the invention is involves a method for operating a cardiac pacing device. An early activation pacing interval is initialized by calculating an optimal AV delay based on intrinsic atrioventricular intervals between an atrial event and a ventricular depolarization for at least one ventricle and determining an atrial to early ventricular activation interval ($AV_{EA}$) between an atrial event and early activation of a ventricular depolarization for the ventricle. The early activation pacing interval for the ventricle is calculated by subtracting the $AV_{EA}$ from the calculated optimal AV delay. The early activation is started responsive to sensing early activation of the ventricle. The ventricle is paced relative to expiration of the early activation pacing interval.

In some implementations, the $AV_{EA}$ is determined based on an interval between an atrial event and a start of a ventricular depolarization, Q*. In some implementations the $AV_{EA}$ is determined based on the interval between an atrial event and a His Bundle depolarization.

The early activation pacing interval may be initiated responsive to sensing early activation of the right or left ventricle. The ventricle paced relative to the expiration of the early activation pacing interval may be the right ventricle, the left ventricle, or both right and left ventricles. If right and left ventricles are paced, the ventricular paces may be delivered to both ventricles simultaneously. Alternatively, the right and left ventricular paces may be separated by an interventricular delay.

An embodiment of the invention is directed to a cardiac rhythm management device that includes electrodes electrically coupled to multiple chambers of a heart and an implantable pulse generator configured to sense cardiac electrical signals and to deliver pacing pulses via the electrodes. Measurement circuitry coupled to the sense circuitry is configured to measure one or more cardiac intervals. The intervals include atrioventricular intervals (AVIs) between an atrial event and a ventricular depolarization for at least one ventricle and an atrial event to early ventricular activation interval ($AV_{EA}$) between an atrial event and early activation of a ventricular depolarization for the ventricle. Optimization circuitry calculates an optimal AV delay based on the measured atrioventricular intervals and calculates an early activation pacing interval for the ventricle by subtracting the measured $AV_{EA}$ from the calculated optimal AVD. A pacing interval controller starts the early activation in response to sensing early activation of the ventricle. Pacing therapy circuitry delivers pacing pulses to the ventricle relative to expiration of the early activation pacing interval.

For example, in one implementation, the atrial to early ventricular activation interval comprises an interval between the atrial event and a start of a ventricular depolarization, Q*. In one embodiment, the atrial to early ventricular activation interval comprises an interval between the atrial event and the His Bundle depolarization.

Yet another embodiment of the invention is directed to a method of operating a cardiac pacing device. An atrial (A-A) interval and an intrinsic atrioventricular interval (AVI) of a first cardiac cycle are measured. A pacing escape interval for a synchronized ventricular chamber is calculated based on the measured A-A interval and the measured AVI. The pacing escape interval is started responsive to sensing an intrinsic ventricular rate chamber depolarization of the first cardiac cycle. During a second cardiac cycle immediately following the first cardiac cycle, a ventricular synchronized chamber is paced relative to expiration of the pacing escape interval. For each subsequent cardiac cycle, the pacing escape interval is recalculating based at least on a measured A-A interval from an immediately previous cardiac cycle.

According to some implementations, the rate chamber is the right ventricle and the synchronized chamber is the left ventricle. Alternatively, the rate chamber may be the left ventricle and the synchronized chamber may be the right ventricle.

In one implementation, the pacing escape interval is based on a difference between the intrinsic atrioventricular interval of the first cardiac cycle and an optimized synchronized chamber atrioventricular delay. In one implementation, the pacing escape interval comprises a difference between an intrinsic atrioventricular interval of the first cardiac cycle and an optimized synchronized chamber atrioventricular delay subtracted from the A-A interval of the first cardiac cycle.

Another embodiment of the invention involves a cardiac rhythm management device. Measurement circuitry of the cardiac rhythm management device measures intervals between atrial events and atrioventricular intervals (AVIs) between an atrial event and a ventricular depolarization. Optimization circuitry calculates a pacing escape interval for a synchronized ventricular chamber based on a measured A-A interval and a measured AVI for a first cardiac cycle. A pacing interval controller starts the pacing escape interval in response to sensing an intrinsic ventricular rate chamber depolarization of the first cardiac cycle. Pacing therapy circuitry delivers pacing to a ventricular synchronized chamber relative to expiration of the pacing escape interval during a second cardiac cycle immediately following the first cardiac cycle. The optimization circuitry is configured to recalculate the pacing escape interval for each subsequent cardiac cycle based at least on a measured A-A interval from an immediately previous cardiac cycle.

For example, in some implementations, the pacing escape interval may be based on a difference between the intrinsic atrioventricular interval of the first cardiac cycle and an optimized synchronized chamber atrioventricular delay. In some implementations, the pacing escape interval comprises a difference between an intrinsic atrioventricular interval of the first cardiac cycle and an optimized synchronized chamber atrioventricular delay subtracted from the A-A interval of the first cardiac cycle.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
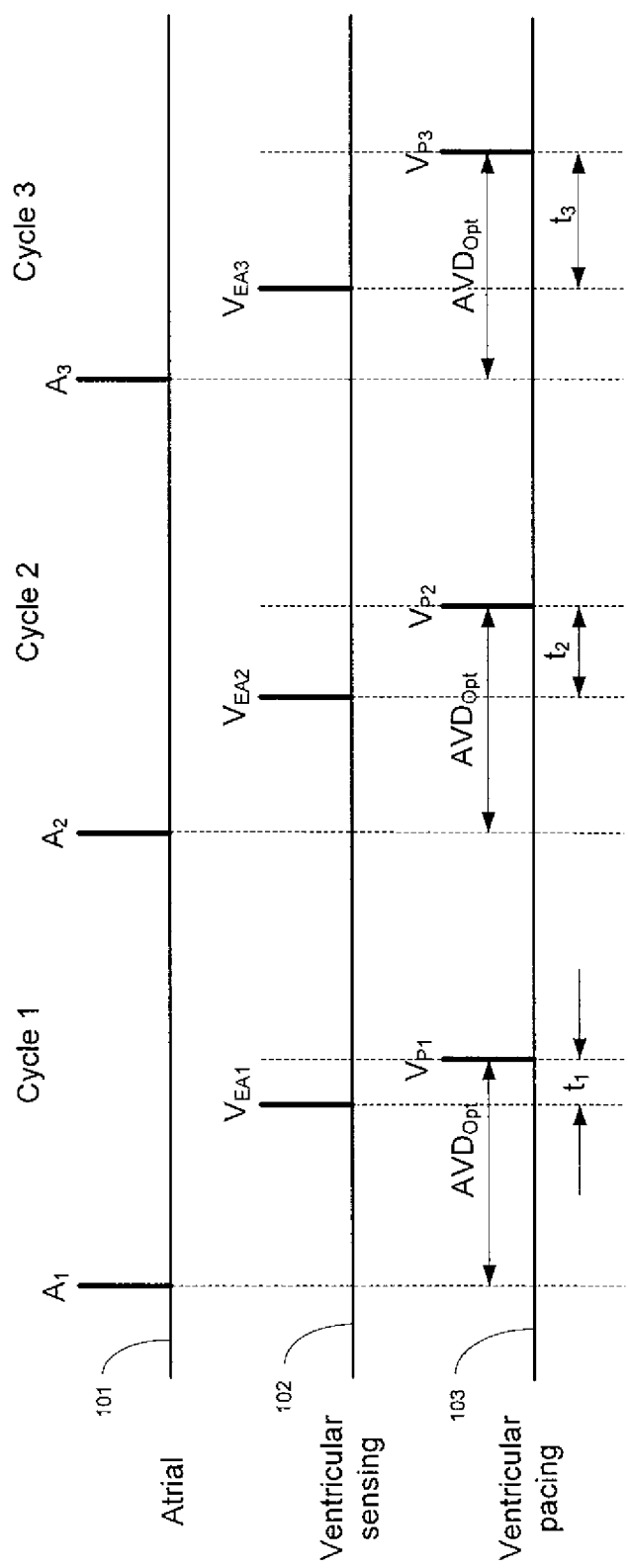
FIG. 1 is a timing diagram that illustrates suboptimal pacing that arises from the use of static pacing delays.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein below. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Mechanical contractions in the heart are triggered by waves of electrical depolarization that travel through the cardiac tissue. In a healthy heart, a depolarization wave for each cardiac cycle is initiated at the sinoatrial node and travels through the AV node, the His bundle, the left and right bundle branches and the Purkinje fibers to cause contractions of the ventricles. Due to age, disease, damage from myocardial infarction, and/or other degradation, the pathways and/or tissues involved in conduction of the depolarization wavefront may become compromised.

Pacemakers deliver electrical pacing pulses to the heart to produce contractions of the heart chambers in synchrony and at a rate sufficient to meet the patient's metabolic demand. Pacing therapy involves the implementation of timing intervals between various events during a cardiac cycle. The timing intervals may be used to control the rate of heart chamber contractions and/or the synchrony between heart chamber contractions. For example, for patients whose intrinsic heart rate is too slow, pacing assists the heart in contracting at a rate that is sufficient to provide blood flow to meet the patient's metabolic requirements. For patients suffering from heart failure (HF), cardiac pacing may be used to ensure that the contractions of the heart chambers occur in a timed sequence that improves heart function.

Pacemakers typically include intracardiac electrodes arranged to be in electrical contact with the myocardium and configured to sense cardiac depolarization signals and/or deliver cardiac pacing pulses in a timed sequence during cardiac cycles. For example, during a cardiac cycle, pacing escape intervals (pacing delays) may be established between a right or left atrial event and a right or left ventricular pace (AVD) and/or between a ventricular event in one chamber and a ventricular event in the opposite chamber (IVD). In applications having bi-atrial sensing and/or pacing capability, a pacing delay may be established between an atrial event in one chamber and an atrial event in the opposite chamber (IAD). One or more of the pacing delays may be adjusted to a predetermined value to enhance the pumping action of the heart. For example, in cardiac resynchronization pacing, the setting of the AVD and/or the IVD and/or the IAD can have a significant impact on hemodynamic function. These pacing escape intervals may be set to promote fusion between the left and right chamber depolarizations and/or to enhance ventricular preload.

Determining optimal pacing intervals, such as the AVD and/or IVD, may involve measurement of intrinsic conduction data while the patient is at rest or at a specified cardiac rate. One technique for determining optimal pacing escape intervals is described in commonly owned U.S. Pat. No. 7,123,960, which is incorporated herein by reference in its entirety.

Over time, previously computed optimal pacing delays may become suboptimal due to changing patient conditions including disease processes, myocardial infarction, and/or other factors which alter the cardiac response. Even if re-optimization is performed, pacing may occur using suboptimal pacing delays during periods between the re-optimization processes Embodiments of the invention are directed to approaches to maintain optimal cardiac resynchronization pacing on a beat-by-beat basis.

Embodiments of the invention are directed to starting pacing delays for one or multiple sites in the RV, one or multiple sites in the LV, or both the RV and the LV, wherein the pacing delays are triggered by early intrinsic activation conducted to the ventricle from the AV node. Early activation may be detected by a variety of approaches, including detecting an initial deflection of the QRS complex, denoted Q*, and/or by detecting an indication of the early activation in a signal sensed at a location proximate to the His bundle.

A number of HF patients have intact AV conduction with LBBB which results in ventricular dyssynchrony due to significantly delayed left ventricular contractions. Cardiac function for these patients can be improved by consistent pacing at one or multiple ventricular sites to achieve fusion between the left ventricular (LV) paced wavefront and the intrinsic conduction from the AV node. In some HF patients, it is advantageous to provide consistent RV pacing at one RV site or multiple RV sites triggered by early activation of the RV. The pacing delay(s) for the pacing site(s) may be timed to fuse depolarization wavefronts from multiple RV sites with an intrinsic depolarization. Pacing to achieve fusion of multiple wavefronts produces a more powerful and/or more coordinated cardiac contraction.

Some embodiments of the invention are directed to LV and/or RV pacing with pacing delays timed relative to an early activation signal, e.g., through detection of Q* in the QRS or His bundle sensing. Some embodiments of the invention are directed to triggered LV pacing using pacing delays based on the timing of a previous intrinsic depolarization of the RV. The approaches described herein provide for beat-by-beat adjustment of LV and/or RV pacing delays to avoid periods of suboptimal pacing which results from using static pacing delays or pacing delays that are optimized periodically.

FIG. 1 illustrates suboptimal pacing that arises from the use of a static pacing delay, e.g., static $AVD_{Opt}$. FIG. 1 illustrates an atrial sensing/pacing channel 101, a ventricular sensing channel 102, and a ventricular pacing channel 103. The three cardiac cycles illustrated, cycle 1, cycle 2, cycle 3, each begin with an intrinsic or paced atrial event $A_1$, $A_2$, $A_3$. For each pacing cycle, an AV pacing delay, $AVD_{Opt}$, is initiated responsive to atrial events $A_1$, $A_2$, $A_3$. Pacing pulses $V_{p1}$, $V_{p2}$, $V_{p3}$ are delivered to one or both ventricles relative to the expiration of the $AVD_{Opt}$ for each cycle. The pacing pulses $V_{p1}$, $V_{p2}$, $V_{p3}$ may be delivered to one ventricle, or may be biventricular. If biventricular pacing is delivered, the right and left ventricular paces may be simultaneous or separated by an interventricular delay.

FIG. 1 illustrates the situation wherein $AVD_{Opt}$ becomes suboptimal over time. In some embodiments, $AVD_{Opt}$ is set to be short enough so that one or both ventricles are consistently paced. To achieve fusion pacing during a cardiac cycle, the ventricular pacing pulse must be delivered at a specific instant in time from early activation of the ventricular depolarization. Cycle 1 represents a cardiac cycle that occurs just after optimization. During Cycle 1, the value of $AVD_{Opt}$ produces a time interval, $t_1$, between the early activation signal $V_{EA1}$ and the ventricular pace $V_{p1}$ that allows for fusion to occur between an intrinsic depolarization and the depolarization evoked by the ventricular pace. Over time, the relative timing of $AVD_{Opt}$ and $V_{EA}$ may shift, causing the interval between $V_{EA}$ and the ventricular pace for the cycle to become longer or shorter. As illustrated in FIG. 1, shifts in $V_{EA2}$ and $V_{EA3}$ causes $t_2$ and $t_3$ to become longer than $t_1$. Changes in the time interval between the early activations $V_{EA2}$, $V_{EA3}$ and the ventricular paces $V_{p2}$, $V_{p3}$ in cycles 2 and 3 can become so great that fusion pacing is precluded. In cycles 2 and 3, pacing is suboptimal because time intervals $t_2$ and $t_3$ are too long to produce fusion.

Figure 2:
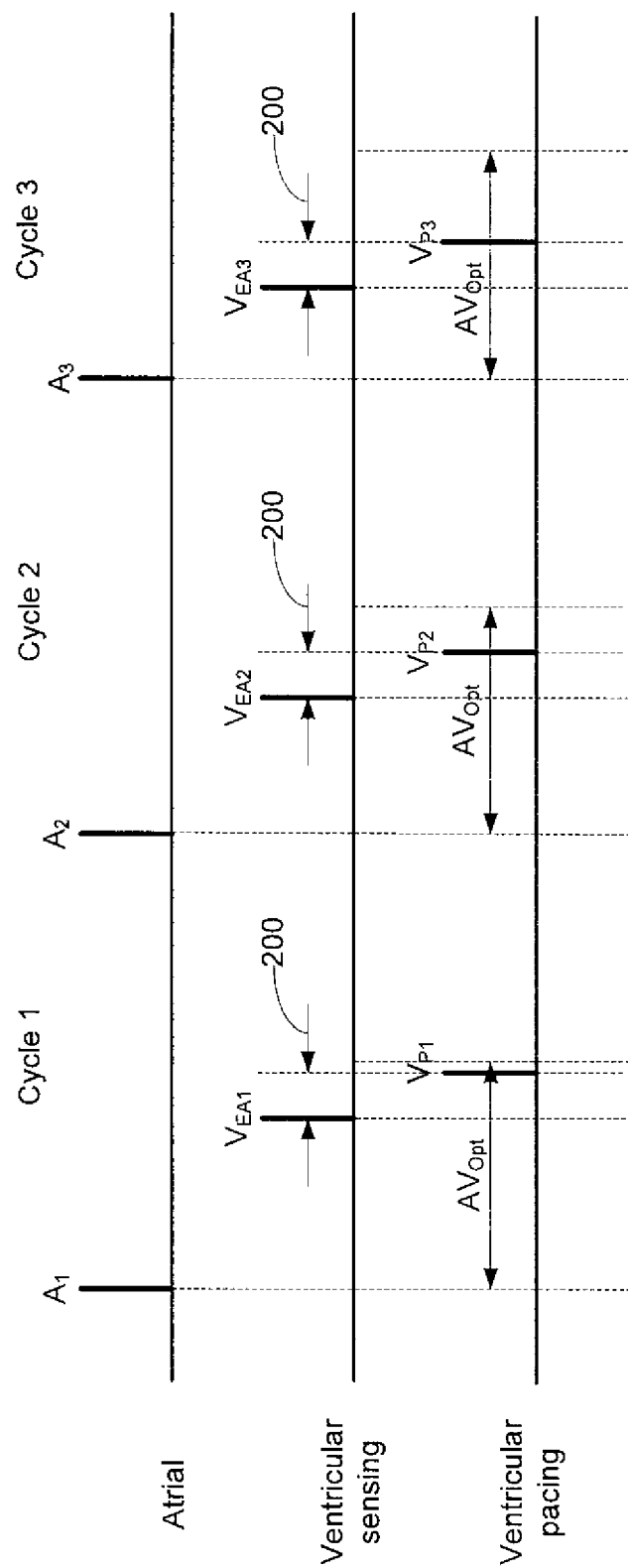
FIG. 2 is a timing diagram having cardiac cycles wherein ventricular pacing is triggered by early activation of the ventricular depolarization in accordance with embodiments of the invention.

Embodiments of the invention are directed to methods and systems configured to maintain a substantially constant time interval between sensed early activation and the delivery of the pacing pulse. The substantially constant time interval between the early activation and pacing is optimized to promote fusion between an intrinsic and paced depolarization wavefronts. FIG. 2 depicts a timing diagram illustrating cardiac cycles wherein ventricular pacing is triggered by early activation of the ventricular depolarization. The early activation of the ventricle may be detected by sensing Q* and/or by sensing an activation at the His bundle, for example. FIG. 2 shows ventricular pacing for three cardiac cycles, cycle 1, cycle 2, cycle 3, beginning with an intrinsic or paced atrial event $A_1, A_2, A_3$. The ventricular pacing pulses $V_{p1}, V_{p2}, V_{p3}$ are delivered independently of the atrial events $A_1, A_2, A_3$ and are triggered in response to sensing ventricular early activation $V_{EA1}, V_{EA2}, V_{EA3}$. The triggered ventricular pacing results in a substantially constant interval 200 between the early activation $V_{EA1}, V_{EA2}, V_{EA3}$ and the ventricular pace $V_{p1}, V_{p2}, V_{p3}$ beat by beat for each cardiac cycle.

The interval $V_{EA} \rightarrow V_p$ 200 used for the cardiac cycles can be adjusted to a value that promotes consistent fusion pacing. As previously described, in some embodiments, detection of early activation, $V_{EA}$, occurs when an initial deflection of the ventricular depolarization Q* is sensed. In these embodiments, the $V_{EA} \rightarrow V_p$ 200 interval is the time interval between Q* and the ventricular pace. In other embodiments, $V_{EA} \rightarrow V_p$ 200 interval is the time interval between a sensed activation at the His Bundle and the ventricular pace. In either approach, the optimal $V_{EA} \rightarrow V_p$ interval may be determined based on intrinsic conduction delays. In one example, the optimal $V_{EA} \rightarrow V_p$ interval is described by the following equation:

$$V_{EA} \rightarrow V_p = AVD_{Opt} - AV_{EA}$$

where $AVD_{Opt}$ is a fixed optimal AV delay and $AV_{EA}$ is an interval between an intrinsic or paced atrial event, A, and the early ventricular activation, $V_{EA}$.

The $AVD_{Opt}$ and $AV_{EA}$ used for computing the pacing interval $V_{EA} \rightarrow V_p$ may be determined in an initialization phase. If biventricular pacing use used, the $V_{EA} \rightarrow V_p$ interval may be different for LV and RV pacing, e.g., there may be a $V_{EA} \rightarrow V_{p1}$, for left ventricular pacing and $V_{EA} \rightarrow V_{pR}$ for right ventricular pacing, where $V_{EA} \rightarrow V_{pL} \neq V_{EA} \rightarrow V_{pR}$. As a safety feature, if there is no intrinsic activity sensed up to a predetermined AV delay, then a backup pace to the RV, the LV or both ventricles can be delivered. Additionally, there may be a minimum interval from atrial event to the ventricular pace that is allowed to reduce the symptoms of pacemaker syndrome.

Figure 3:
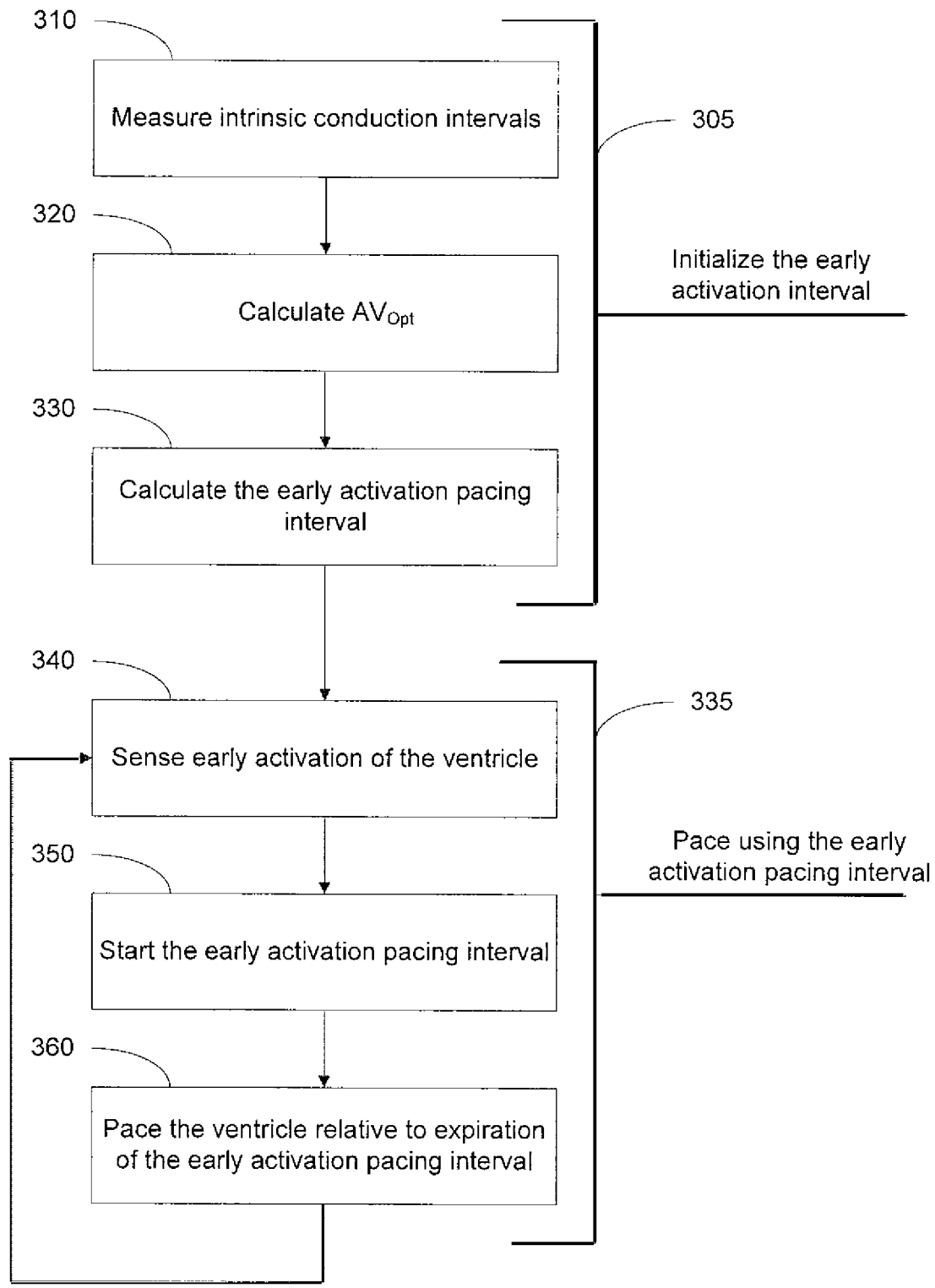
FIG. 3 is a flow diagram that illustrates a process for pacing based on early ventricular activation in accordance with embodiments of the invention.

FIG. 3 is a flow diagram that exemplifies a process for pacing based on early ventricular activation. The process includes computing $V_{EA} \rightarrow V_p$ based on the measured conduction delay ($AV_{EA}$) between the atrial event, A, and the early ventricular activation, $V_{EA}$, and $AVD_{Opt}$. In some embodiments, $AVD_{Opt}$ is calculated as a fraction of a measured intrinsic AV interval (AVI), e.g., the right ventricular AVI, denoted $AVI_R$. In some embodiments, the $AVD_{Opt}$ is calculated as a linear combination of the right AVI ($AVI_R$) and the intrinsic left AVI ($AVI_L$).

During the initialization phase 305, various conduction intervals are measured 310, e.g., $AV_{EA}$, QRS width, $AVI_L$, $AVI_R$. $AVD_{Opt}$ is determined 320 based on one or more of the measured conduction intervals and/or empirically measured coefficients. The measured conduction delays for the $AV_{EA}$ interval and/or the conduction intervals used in calculation of $AVD_{Opt}$ may be determined using a single measurement of a conduction interval or may be determined using a combination of multiple measured intervals. The early activation pacing delay $V_{EA} \rightarrow V_p$ is calculated 330 based on the $AV_{EA}$ and $AVD_{Opt}$.

Pacing is delivered 335 using the $V_{EA} \rightarrow V_p$ delay interval. Early activation of the ventricle may be determined based on an initial deflection of the QRS complex, or activation sensed at the His bundle, for example.

Q* detection may be based on comparison of the ventricular electrogram to a preestablished template. In one method, a Q* template is established by averaging a number of initial electrogram waveforms. Q* is then established form the average waveform. Averaging the initial electrogram waveforms can be performed by aligning a number, M, of QRS complexes having similar morphology at the peak of the R-wave. For example, M may be a number between about 20 and about 50. The QRS complexes selected for averaging may be identified by the device or by visual inspection. Various methods of determining Q* from the averaged waveform may be implemented.

For example, the absolute derivative of the average waveform may be calculated and the results normalized by the maximum derivative. An algorithm in accordance with one embodiment would then mark the location of the R-wave of the average waveform by searching for a largest peak.

Another method of identifying Q* involves searching for a flat segment of the normalized derivative prior to the R-wave. The search may be performed by calculating the mean and standard deviation (STD) of data points within a fixed-length window that moves away from the location of R-wave to the left (i.e. earlier than R-wave). The data related to the flattest segment of the normalized derivative has the minimum standard deviation over all the data within the window. The window length can be programmed to values between about 20 to about 100 ms. The algorithm may then set a threshold as the mean+STD of the flat segment. The algorithm would then start from the flat segment, examine each data point in the normalized derivative and compare it with the threshold. The Q* point is established as the first point after which there are no more than M consecutive data points whose values fall below the threshold. Typically, M is set to be a number that spans about 2 ms to about 5 ms in time. In one embodiment, the M value has been set to be equivalent to 4 ms. The location of Q* is then identified in the original averaged waveform.

The Q* template is established as a segment of data from the original averaged waveform extending for a time $T_1$ prior to the Q* point and a time $T_2$ following the Q* point. $T_1$ and $T_2$ can be programmed to fall in a range of about 10 to about 100 ms.

After establishment of the template, subsequent cardiac signals are compared to the template. The search for a Q* point may begin about 200 ms after the R-wave of the previous beat (intrinsic) or 300 ms after the pacing pulse of the previous (stimulated) beat. Each incoming data point in the electrogram and all the past data points within a window (length=$T_1+T_2$) are cross-correlated with the template to identify Q*. Additional details regarding Q* detection are described in commonly owned U.S. Pat. No. 6,768,923 which is incorporated herein by reference.

Activation of the His bundle may be implemented by sensing for the His depolarization during a His signal sensing window following the atrial event in each cardiac cycle. The onset and/or duration of the His signal sensing window may be programmable. In one embodiment, His bundle activation is indicated by detecting a peak of the His signal.

Upon sensing 340 early activation of the ventricle, the early activation pacing interval $V_{EA} \rightarrow V_p$ is initiated 350. Ventricular pacing to one or both ventricles is delivered 360 relative to expiration of the $V_{EA} \rightarrow V_p$.

$AVD_{Opt}$ may be calculated during the initialization phase based on the measured conduction delay between an atrial event, A, and the right ventricular activation ($AVI_R$) and/or the conduction delay between an atrial event and the left ventricular activation, ($AVI_S$), and/or other conduction delays, e.g., the conduction delay between right and left ventricular activations.

In some embodiments, $AVD_{Opt}$ for a particular patient may be estimated as a fraction of the $AVI_R$, where the fraction used is based on the width of the patient's intrinsic QRS waveform. Using this technique, $AVD_{Opt}$ may be calculated as follows:

$AVD_{Opt=N1} AVI + K_{narrow}$, for patients having a narrow QRS complex; and $AVD_{Opt=N2} AVI + K_{wide}$, for patient having a wide QRS complex, where $0 < N_1, N_2 < 1$ and $N_2 \leq N_1$, and $K_{narrow}$ and $K_{wide}$ may be empirically determined constants.

Values for $N_1$ may be in a range of about 0.6 to about 0.8, and values for $N_2$ may be in a range of about 0.4 to about 0.6, for example. A narrow QRS complex is one having a width of less than about 150 ms, and a wide QRS complex is on have a width greater than 150 ms.

In some embodiments, $AVD_{Opt}$ for a particular patient may be estimated from approximated conduction delays in terms of specified coefficients $K_T$, as:

$$AVD_{Opt} = K_1 AV_L + K_2 AV_R + K_3$$

Derivation of the specified coefficients, $K_n$ or $N_n$ for later programming into the system or for use by a clinician, involves obtaining clinical population data related to particular values of the measured conduction parameters to an optimum value of the pacing parameter as determined by concurrent measurement of another parameter reflective of cardiac function (e.g., maximum dP/dt). A linear regression analysis may be performed to derive values of the specified coefficients used in the formula for setting the pacing parameter, the specified coefficients thus being regression coefficients.

As previously discussed, the techniques for determining $AVD_{Opt}$ and/or $AV_{EA}$ as described herein, may be implemented in a number of different ways. In one implementation, a system for determining the $V_{EA} \rightarrow V_p$ pacing interval includes an external programmer. In an example embodiment, one or more intrinsic conduction parameters, as measured from electrogram signals generated by the sensing channels of an implantable cardiac resynchronization device during intrinsic beats, are transmitted to the external programmer via a wireless telemetry link. The measured conduction data, such as the atrial event to $V_{EA}$ interval, $AV_R$, $AV_L$, and/or QRS width, may represent averages of values obtained during a specified number of beats. The external programmer then computes the optimal $V_{EA} \rightarrow V_p$ based on a computed $AVD_{Opt}$ and measured $AV_{EA}$. In an automated system, the external programmer then automatically programs the implantable device with the computed $V_{EA} V_p$ interval, while in a semi-automated system the external programmer presents the computed $V_{EA} V_p$ interval to a clinician in the form of a recommendation.

In another automated application, an automated system may also be made up of the implantable device alone which collects conduction data, measures $AV_{EA}$, computes the $AVD_{Opt}$, and then computes the $V_{EA} V_p$ accordingly.

In another embodiment, which may be referred to as a manual system, the external programmer presents the collected intrinsic conduction data to a clinician who then programs the implantable device with parameters computed from the intrinsic conduction data by, for example, using a printed lookup table and procedure. Unless otherwise specified, references to a system for computing or setting pacing parameters throughout this document should be taken to include any of the automated, semi-automated, or manual systems just described.

Some embodiments of the invention are directed to a process for pacing a synchronized chamber (left ventricle) using a pacing delay initiated by an intrinsic rate chamber (right ventricle) depolarization. Typically, the AV nodal conduction is gradual and does not change significantly within a beat. Based on this assumption, the technique used in this embodiment can maintain the beat to beat $Vp_L$ to $Vs_{Rf}$ interval to be substantially constant.

Figure 4:
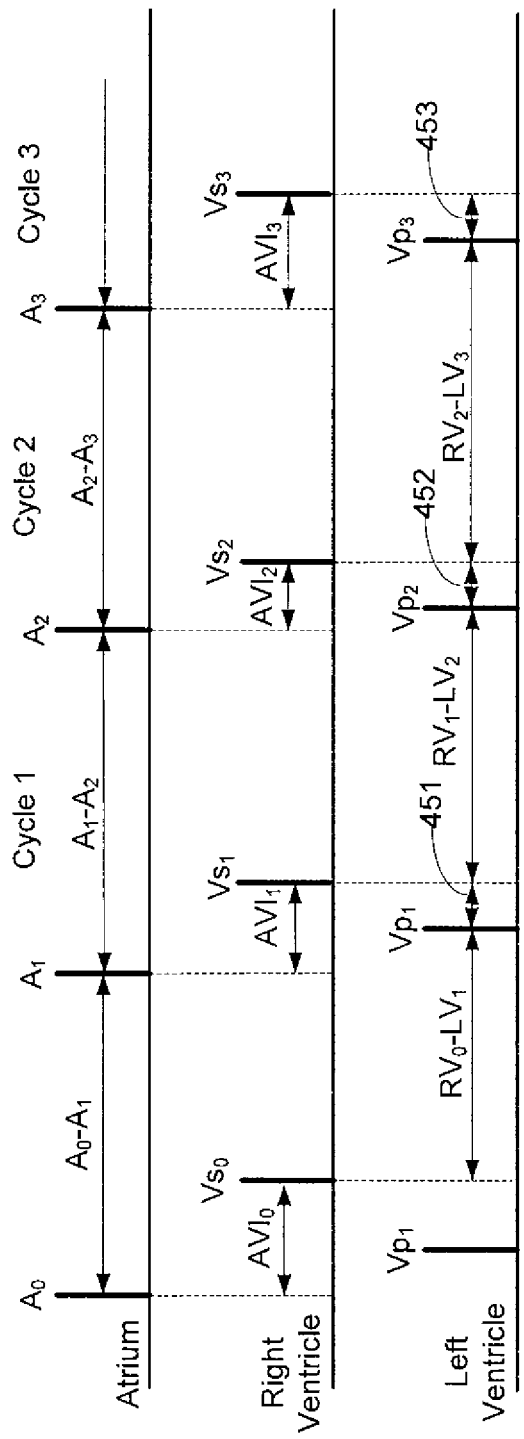
FIG. 4 is a timing diagram that illustrates pacing the synchronized ventricular chamber in accordance with embodiments of the invention.

FIG. 4 is a timing diagram that illustrates pacing the synchronized ventricular chamber in accordance with embodiments of the invention. The timing diagram illustrates an initial cardiac cycle initiated by atrial event $A_0$ followed by three cardiac pacing cycles, cycle 1, cycle 2, cycle 3 initiated by atrial events $A_1, A_2, A_3$. During cycle 1, the LV pace $Vp_1$ is delivered following a pacing escape interval $RV_0$-$LV_1$ that is initiated by the right ventricular sense $Vs_0$ of the previous cycle. During cycle 2, the LV pace $Vp_2$ is delivered following a pacing escape interval $RV_1$-$LV_2$. During cycle 3, the LV pace $Vp_3$ is delivered following a pacing escape interval $RV_2$-$LV_3$.

Initiating the pacing escape interval $RV_{n-1}$-$LV_n$ from an intrinsic RV depolarization enhances fusion pacing of the LV during the following beat. The pacing delay $RV_{n-1}$-$LV_n$ may change on a beat by beat basis or within a certain number of beats that have a change in cycle length. Initiation of the $RV_{n-1}$-$LV_n$ pacing delay responsive to the intrinsic RV depolarization results in beat by beat alterations in the timing of the LV pace. These beat by beat alterations in the LV pace timing compensate for gradual changes in the timing of the RV depolarizations so that the $Vp_n$ to $Vs_n$, intervals 451, 452, 453 in each cycle remains relatively constant and fusion pacing is maintained.

Figure 5:
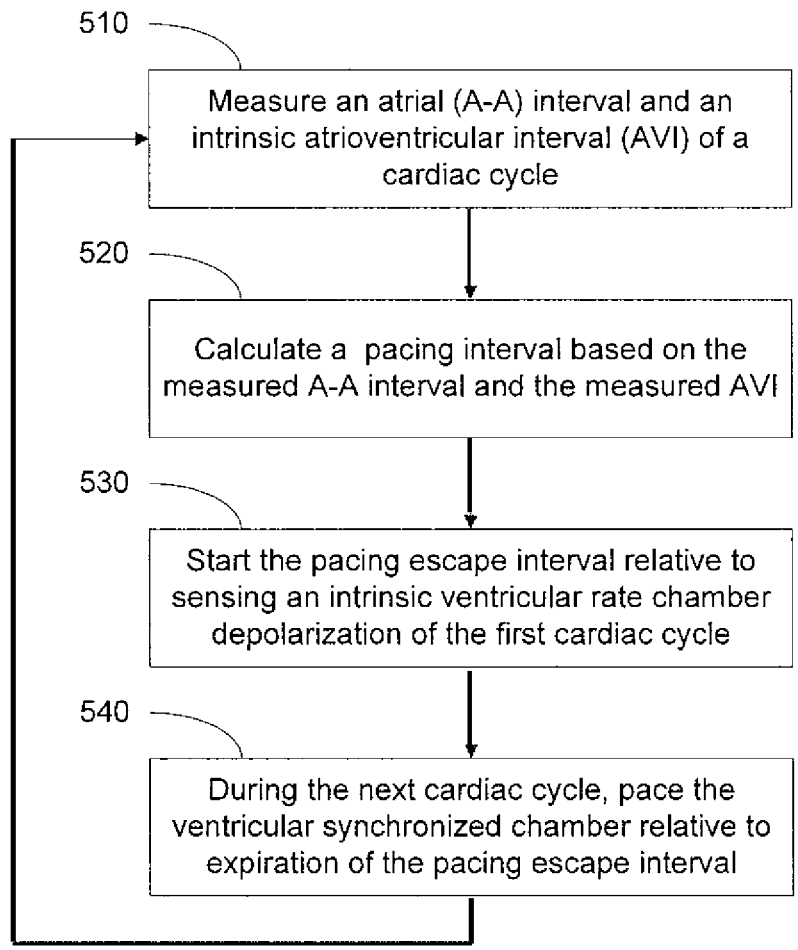
FIG. 5 is a flow diagram illustrating a process of pacing using an optimized pacing delay for an LV pace that is initiated by an intrinsic RV depolarization occurring in an immediately preceding cardiac cycle in accordance with embodiments of the invention.

FIG. 5 is a flow diagram illustrating a process of pacing using an optimized pacing delay for an LV pace ($RV_{n-1}$-$LV_n$) that is initiated by an intrinsic RV depolarization occurring in an immediately preceding cardiac cycle. During an initialization stage, the pacing delay $RV_{n-1}$-$LV_n$ may be initially optimized based on measured intervals to achieve optimal coordination between intrinsic RV depolarizations and LV paced depolarizations. In this embodiment, the $RV_{n-1}$-$LV_n$ interval is initially optimized using measured atrial interval (A-A) data and intrinsic RV atrioventricular interval ($AVI_R$) data from one or more cardiac cycles. The A-A interval between a paced or intrinsic atrial depolarization of a first cardiac cycle and the paced or intrinsic atrial depolarization of the immediately subsequent cardiac cycle and the $AVI_R$ are measured 510 for one or more cardiac cycles. An LV pacing escape interval is calculated 520 based on the measured A-A interval and the measured $AVI_R$. In one embodiment, the LV pacing escape interval, $RV_{n-1}$-$LV_n$, may be calculated as follows:

$$RV_{n-1}\text{-}LV_n = (A\text{-}A)_{n-1} - (AVI_{Rn-1} - AVD_{Opt}),$$

where $AVD_{Opt}$ may be calculated as previously described.

The pacing escape interval, $RV_{n-1}$-$LV_n$, is started 530 relative to sensing an intrinsic RV depolarization of a first cardiac cycle. On the next cardiac cycle, the LV is paced 540 relative to expiration of the $RV_{n-1}$-$LV_n$ interval. $AVI_{Rn-1}$-$AVD_{Opt}$ is a constant that is determined during initialization and can be periodically re-determined. The $RV_{n-1}$-$LV_n$ interval may change on beat by beat basis due at least in part to changes in the A-A interval.

Figure 6A:
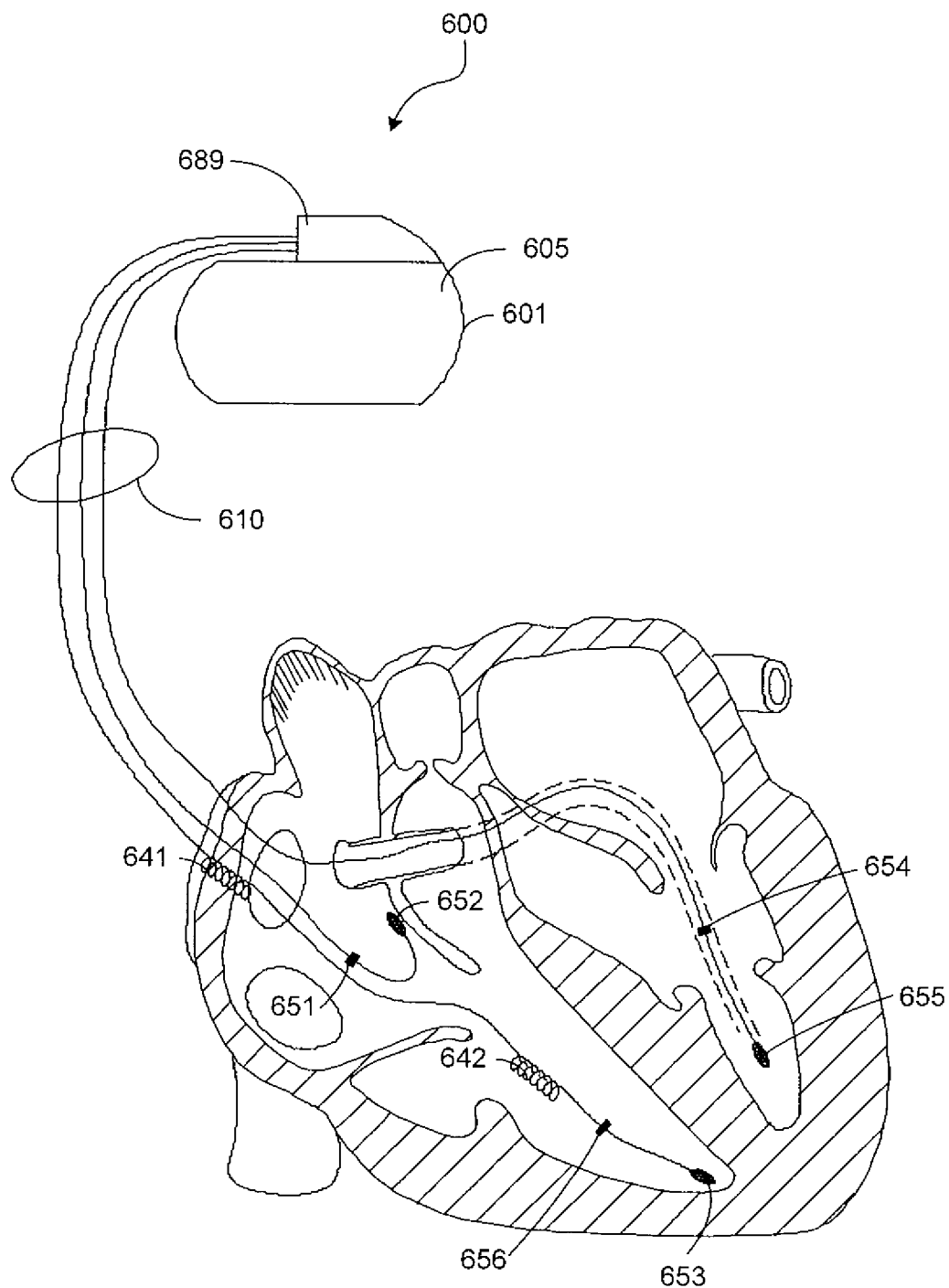
FIG. 6A shows an embodiment of a therapy device that may be used to deliver pacing therapy in accordance with embodiments of the invention.

FIG. 6A illustrates an embodiment of a therapy device 600 that may be used to deliver pacing therapy in accordance with embodiments of the invention. The therapy device 600 includes a pulse generator 605 electrically and physically coupled to an intracardiac lead system 610. Portions of the intracardiac lead system 610 are inserted into the patient's heart.

The intracardiac lead system 610 includes one or more electrodes configured to sense electrical cardiac activity of the heart and deliver electrical stimulation to the heart. Additionally, the cardiac electrodes and/or other sensors may be used to sense the patient's transthoracic impedance, and/or sense other physiological parameters, such as cardiac chamber pressure or temperature.

Portions of the housing 601 of the pulse generator 605 may optionally serve as one or multiple can or indifferent electrodes. The housing 601 is illustrated as incorporating a header 689 that may be configured to facilitate removable attachment between one or more leads and the housing 601.

The lead system 610 includes one or more cardiac pace/sense electrodes 651-656 positioned in, on, or about one or more heart chambers for sensing electrical signals from the patient's heart and/or delivering pacing pulses to the heart. The intracardiac sense/pace electrodes 651-656, such as those illustrated in FIG. 6A, may be used to sense and/or pace one or more chambers of the heart, including the left ventricle, the right ventricle, the left atrium and/or the right atrium. The lead system 610 may include one or more defibrillation electrodes 641, 642 for delivering defibrillation/cardioversion shocks to the heart.

The pulse generator 605 includes circuitry, such as filters, amplifiers, digitizers and/or other signal processing circuitry, used in conjunction with the cardiac electrodes 651-656 for sensing cardiac electrical signals. Various signal features may be extracted and/or measured from the sensed cardiac signals, including R-waves, QRS features, and/or Q* deflections. Pacing controller circuitry disposed within the pulse generator 605 may incorporate circuitry capable of measuring various intrinsic conduction intervals and other cardiac intervals such as intrinsic right and/or left atrioventricular intervals, A-A intervals, V-V intervals, QRS widths, interatrial and/or interventricular conduction delays.

In some embodiments, the pacing controller circuitry is configured to measure and use intrinsic conduction data to determine optimal pacing delays such as $AVD_{Opt}$, $Q^*$-$V_p$, and/or $RV_{n-1}$-$LV_n$ as described in more detail above. In some embodiments, the pulse generator 605 transfers sensed or derived information relevant to the determination of pacing delays to a patient-external device (not shown). Following download of the implantably sensed or derived information, determination of optimal pacing timing delays may be made by the patient-external device or may be made by a human analyst. The pacing delays are then transferred to the therapy device 600 and used to control the timing of pacing pulses delivered to the heart.

Communications circuitry is disposed within the housing 601 for facilitating communication between the pulse generator 605 and a patient-external device, such as an external programmer or advanced patient management (APM) system, for example. The communications circuitry may also facilitate unidirectional or bidirectional communication with one or more implanted, external, cutaneous, or subcutaneous physiologic or non-physiologic sensors, patient-input devices and/or information systems.

The lead system 610 and pulse generator 605 may incorporate one or more sensors, such as a transthoracic impedance sensor and/or an accelerometer which can be used to acquire information related to the patient's hemodynamic need and/or movement. Information from these sensors may be used to adapt the rate of pacing to the patient's level of activity and/or hemodynamic requirements.

Figure 6B:
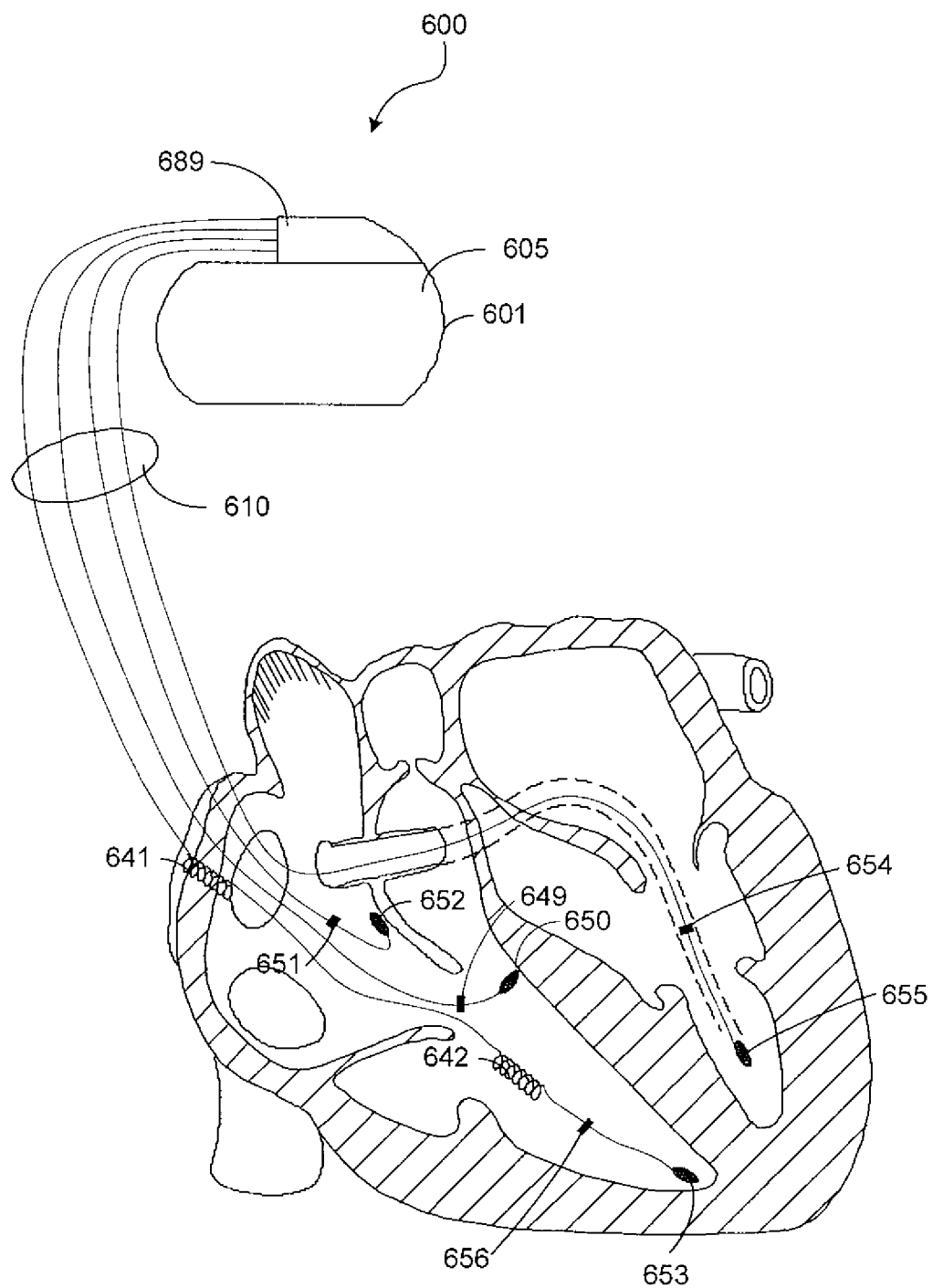
FIG. 6B illustrates an embodiment of a therapy device for delivering pacing therapy including a His lead having a His electrode arranged to sense His bundle depolarizations in accordance with embodiments of the invention.

FIG. 6B illustrates an embodiment of a therapy device 600 that includes a pulse generator 605 and lead system as in FIG. 6A with the addition of a His lead having a His electrode 650 arranged to sense His bundle depolarizations. The His lead may additionally incorporate a His ring electrode 649 which provides for bipolar sensing of His bundle activations. During implantation, the His bundle may be located through tissue impedance measurements to facilitate placement of the His electrodes 649, 650.

Figure 7:
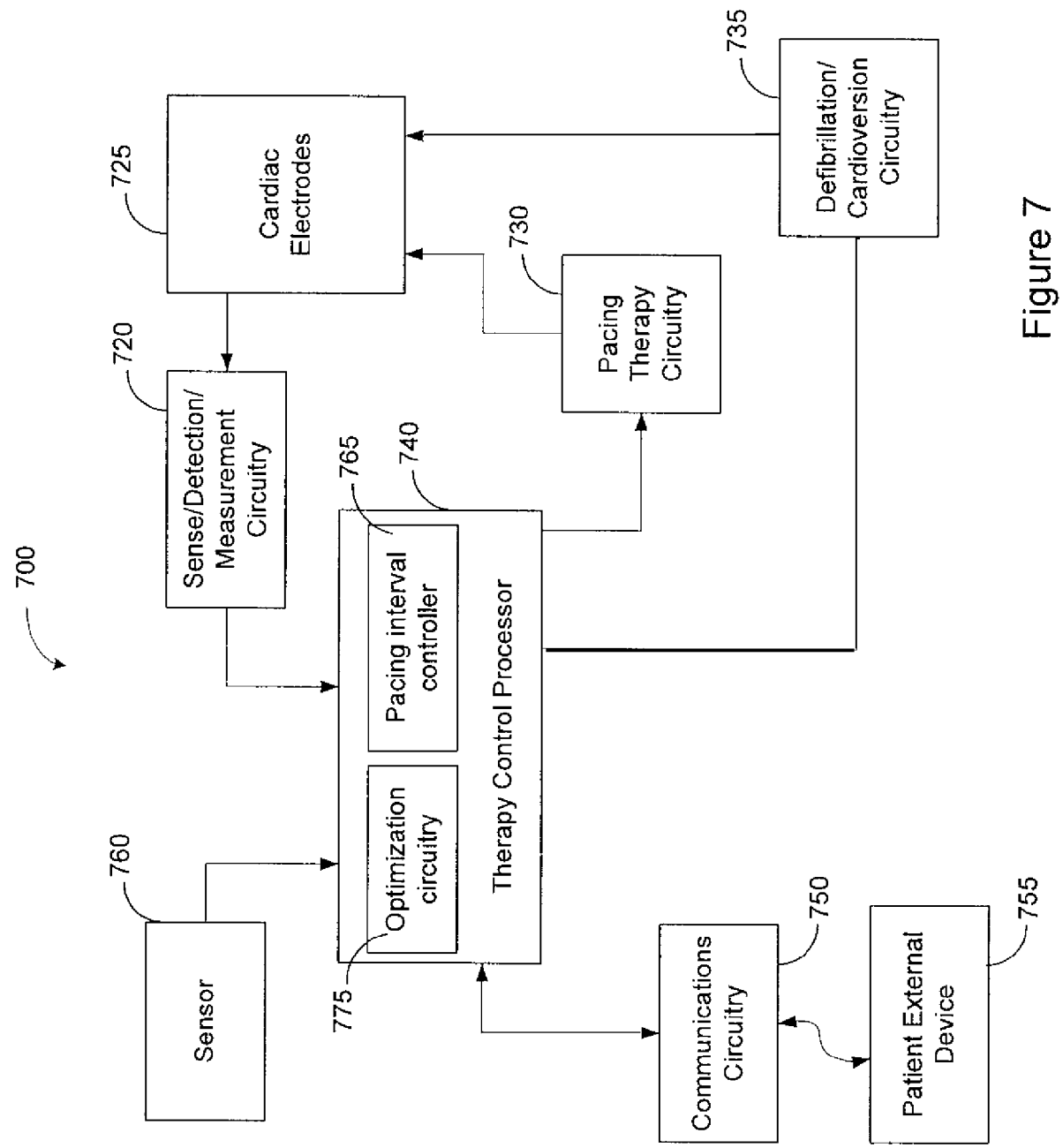
FIG. 7 is a block diagram depicting various components of a system that may be used to deliver pacing therapy in accordance with embodiments of the invention.

FIG. 7 is a block diagram depicting various components of a system that may be used to deliver pacing therapy in accordance with embodiments of the invention. The components, functionality, and configurations depicted are intended to provide an understanding of various features and combinations of features that may be incorporated in such a system. It is understood that a wide variety of device configurations are contemplated, ranging from relatively sophisticated to relatively simple designs. As such, particular configurations may include some components illustrated in FIG. 7, while excluding other components. In certain embodiments, the arrangement of the functional blocks may vary from the arrangement depicted.

The system illustrated in FIG. 7 provides functionality for timing delivery of pacing pulses based sensed early activation of a heart chamber. In some configurations, LV pacing delays may be timed from intrinsic RV depolarizations of a prior cardiac cycle. In some embodiments, the functionality to measure intrinsic conduction and/or optimize pacing delays is incorporated into an implantable device. In other embodiments, the functionality may be incorporated in the patient-external programmer. In yet other embodiments, the functionality may be divided between a patient implantable device and a patient external device.

The therapy system 700 illustrated in FIG. 7 includes a therapy control processor 740 configured to control pacing therapy circuitry 730 to generate pacing stimulations applied via the cardiac electrodes 725. The therapy control processor 740 may also control high energy shocks produced by the defibrillation/cardioversion circuitry 735 for treating tachyarrhythmia.

Cardiac signals are sensed using cardiac electrodes 725. The sensed cardiac signals are received by sensing circuitry 720, which includes circuitry and for amplifying, filtering and/or digitizing the cardiac signals. The sensed cardiac signals may optionally be processed by noise reduction circuitry (not shown), which may reduce noise and or increase the signal to noise ratio (SNR) of the signals before signals are sent to the control processor 740.

Circuitry 720 may be configured to detect various cardiac signal features, such as R-waves, A-waves, QRS complexes, Q* deflections, His bundle activations, and/or other cardiac signal features. Circuitry 720 may also be configured to measure intrinsic conduction intervals and other cardiac intervals, including intrinsic atrioventricular intervals (left and/or right), QRS widths, A-A intervals, V-V intervals and/or other cardiac intervals. Information from circuitry 720 is input to a therapy control processor 740. Using conduction information from circuitry 720, the optimization circuitry 775 calculates optimal pacing delays. Pacing interval controller 765 times the optimal pacing delays which are initiated responsive to specific cardiac events, e.g., Q* and/or His bundle activation.

The therapy control processor 740 may include arrhythmia detection circuitry such as a signal processor that coordinates analysis of the sensed cardiac signals and/or other sensor inputs to detect cardiac tachyarrhythmia. Rate based and/or morphological discrimination algorithms may be implemented by the control processor 740 to detect and verify the presence and severity of an arrhythmic episode. If arrhythmia is detected, the therapy control processor 740 may coordinate delivery of an appropriate therapy, such as anti-tachyarrhythmia pacing therapy (ATP), cardioversion, and/or defibrillation via the defibrillation/cardioversion circuitry 735 to terminate or mitigate the arrhythmia.

Communications circuitry 750 is coupled to the control processor 740. The communications circuitry 750 allows communication between devices, such as patient-external devices 755 and patient-implantable devices. In one configuration, the communications circuitry 750 and the patient-external device 755 use a wire loop antenna and a radio frequency telemetric link, as is known in the art, to receive and transmit signals and data between the patient-external device 755 and communications circuitry 750. In this manner, programming commands and data may be transferred to the control processor 740 from the patient-external device 755 during and after implant. Using a patient-external programmer, a physician is able to set or modify various parameters used by the therapy control processor 740. For example, a physician may set or modify parameters affecting monitoring, detection, pacing, and defibrillation functions of the therapy control processor 740.

In certain embodiments, the control processor 740 transmits information for determination of pacing timing to the patient-external device 755. The information may include, for example, cardiac electrical signals, markers indicating the timing of certain features or points, measured characteristics or features of the signals, and/or other information. The patient-external device 755 may use the transmitted information to determine pacing timing intervals or may format and display information to facilitate the determination of pacing delays by a human analyst.

Processes for timing the delivery of pacing pulses based on early activation in accordance with embodiments of the invention may be implemented by an implantable device, by a patient-external device, such as a programmer or advanced patient management system, or by a manually implementable procedure, such as by using a printed table lookup to compute the optimal values, and/or by any combination of these techniques.

In one embodiment, the patient-external programmer 755 communicates with the control processor 740 over a telemetry link and receives either raw electrogram data, markers corresponding to particular sensed events, and/or measurements of intervals between sensed events or feature widths as computed by the implantable device. The external programmer 755 may then compute optimal settings for pacing timing intervals which are either transmitted to the control processor 740 for immediate reprogramming or presented to a clinician operating the external programmer as recommendations.

In another embodiment, the external programmer 755 may present the data, markers, and/or measurements to a human analyst who then programs the control processor 740 in accordance with an algorithm. In yet a further embodiment, determination of the pacing timing may be fully automatic and performed by an implantable therapy device.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac pacing device, comprising:
    measuring an atrial (A-A) interval and an intrinsic atrioventricular interval (AVI) of a first cardiac cycle;
    calculating a pacing escape interval for a synchronized ventricular chamber based on the measured A-A interval and the measured AVI;
    starting the pacing escape interval in response to sensing an intrinsic ventricular rate chamber depolarization of the first cardiac cycle;
    during a second cardiac cycle immediately following the first cardiac cycle, pacing a ventricular synchronized chamber relative to expiration of the pacing escape interval; and
    for each subsequent cardiac cycle, recalculating the pacing escape interval based at least on a measured A-A interval from an immediately previous cardiac cycle.

2. The method of claim 1, wherein the rate chamber is a right ventricle and the synchronized chamber is a left ventricle.

3. The method of claim 1, wherein the rate chamber is a left ventricle and the synchronized chamber is a right ventricle.

4. The method of claim 1, wherein calculating the pacing escape interval is based on calculating a difference between the intrinsic atrioventricular interval of the first cardiac cycle and an optimized synchronized chamber atrioventricular delay.

5. The method of claim 1, wherein calculating the pacing escape interval comprises calculating a difference between an intrinsic atrioventricular interval of the first cardiac cycle and an optimized synchronized chamber atrioventricular delay subtracted from the A-A interval of the first cardiac cycle.

6. A method of operating a cardiac rhythm management device, comprising:
    electrically coupling electrodes to multiple chambers of a heart;
    sensing cardiac electrical signals via the electrodes and detecting cardiac signal features associated with cardiac events;
    measuring one or more cardiac intervals, including intervals between atrial events and atrioventricular intervals (AVIs) between an atrial event and a ventricular depolarization;
    calculating a pacing escape interval for a synchronized ventricular chamber based on a measured A-A interval and a measured AVI for a first cardiac cycle;
    starting the pacing escape interval in response to sensing an intrinsic ventricular rate chamber depolarization of the first cardiac cycle;
    pacing a ventricular synchronized chamber relative to expiration of the pacing escape interval during a second cardiac cycle immediately following the first cardiac cycle; and
    recalculating the pacing escape interval for each subsequent cardiac cycle based at least on a measured A-A interval of an immediately previous cardiac cycle.

7. The method of claim 6, wherein pacing the ventricular synchronized chamber comprises delivering right and left ventricular paces substantially simultaneously.

8. The method of claim 6, wherein pacing the ventricular synchronized chamber comprises sequentially delivering right and left ventricular paces separated by an interventricular delay.

* * * * *